(12) United States Patent
Gerald, II et al.

(10) Patent No.: US 8,310,235 B1
(45) Date of Patent: Nov. 13, 2012

(54) NMR APPARATUS FOR IN SITU ANALYSIS OF FUEL CELLS

(75) Inventors: Rex E. Gerald, II, Brookfield, IL (US); Jerome W. Rathke, Homer Glen, IL (US)

(73) Assignee: U.S. Department of Energy, Washington, DC (US)

(*) Notice: Subject to any disclaimer, the term of this patent is extended or adjusted under 35 U.S.C. 154(b) by 1397 days.

(21) Appl. No.: 11/941,385

(22) Filed: Nov. 16, 2007

Related U.S. Application Data

(60) Provisional application No. 60/859,659, filed on Nov. 17, 2006.

(51) Int. Cl.
*G01V 3/00* (2006.01)

(52) U.S. Cl. .................................. 324/321; 324/300

(58) Field of Classification Search .......... 324/300–322; 362/607; 315/158; 250/505
See application file for complete search history.

(56) References Cited

U.S. PATENT DOCUMENTS

| | | | |
|---|---|---|---|
| 5,397,989 A * | 3/1995 | Spraul et al. | 324/321 |
| 6,177,798 B1 * | 1/2001 | Haner et al. | 324/321 |
| 6,191,583 B1 * | 2/2001 | Gerald et al. | 324/318 |
| 6,396,274 B1 * | 5/2002 | Commens et al. | 324/321 |
| 6,972,568 B2 * | 12/2005 | Haner et al. | 324/321 |
| 2011/0227487 A1 * | 9/2011 | Nichol et al. | 315/158 |
| 2011/0229743 A1 * | 9/2011 | Hsu et al. | 429/7 |

* cited by examiner

*Primary Examiner* — Brij Shrivastav
(74) *Attorney, Agent, or Firm* — Bradley W. Smith; Daniel Park; John T. Lucas

(57) ABSTRACT

The subject apparatus is a fuel cell toroid cavity detector for in situ analysis of samples through the use of nuclear magnetic resonance. The toroid cavity detector comprises a gastight housing forming a toroid cavity where the housing is exposed to an externally applied magnetic field $B_0$ and contains fuel cell component samples to be analyzed. An NMR spectrometer is electrically coupled and applies a radiofrequency excitation signal pulse to the detector to produce a radiofrequency magnetic field $B_1$ in the samples and in the toroid cavity. Embedded coils modulate the static external magnetic field to provide a means for spatial selection of the recorded NMR signals.

6 Claims, 9 Drawing Sheets

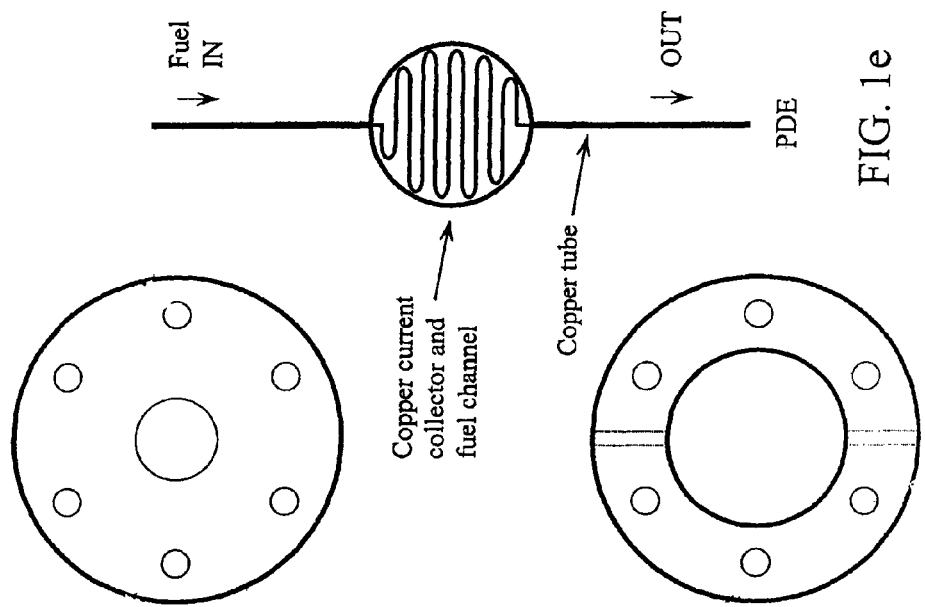
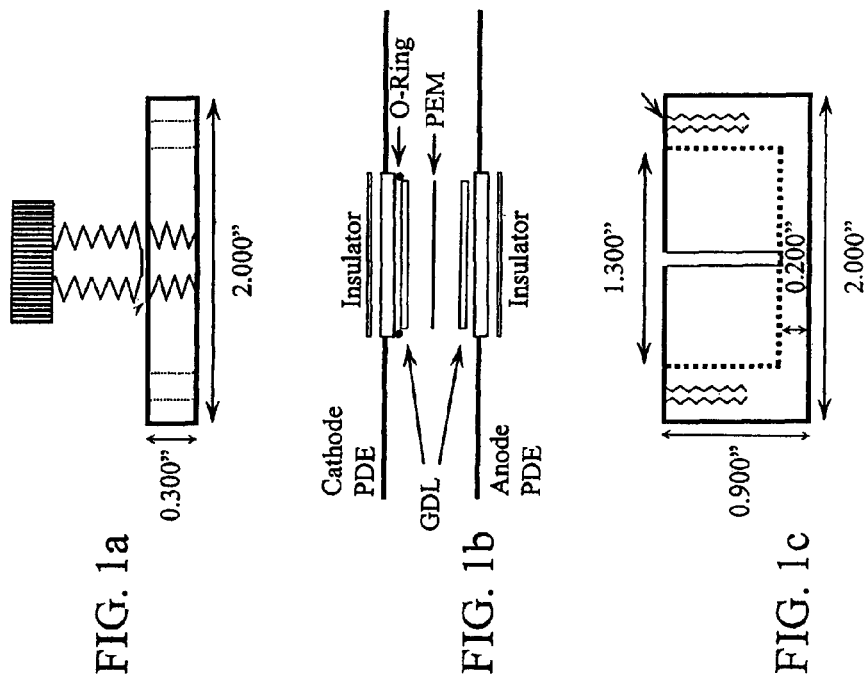

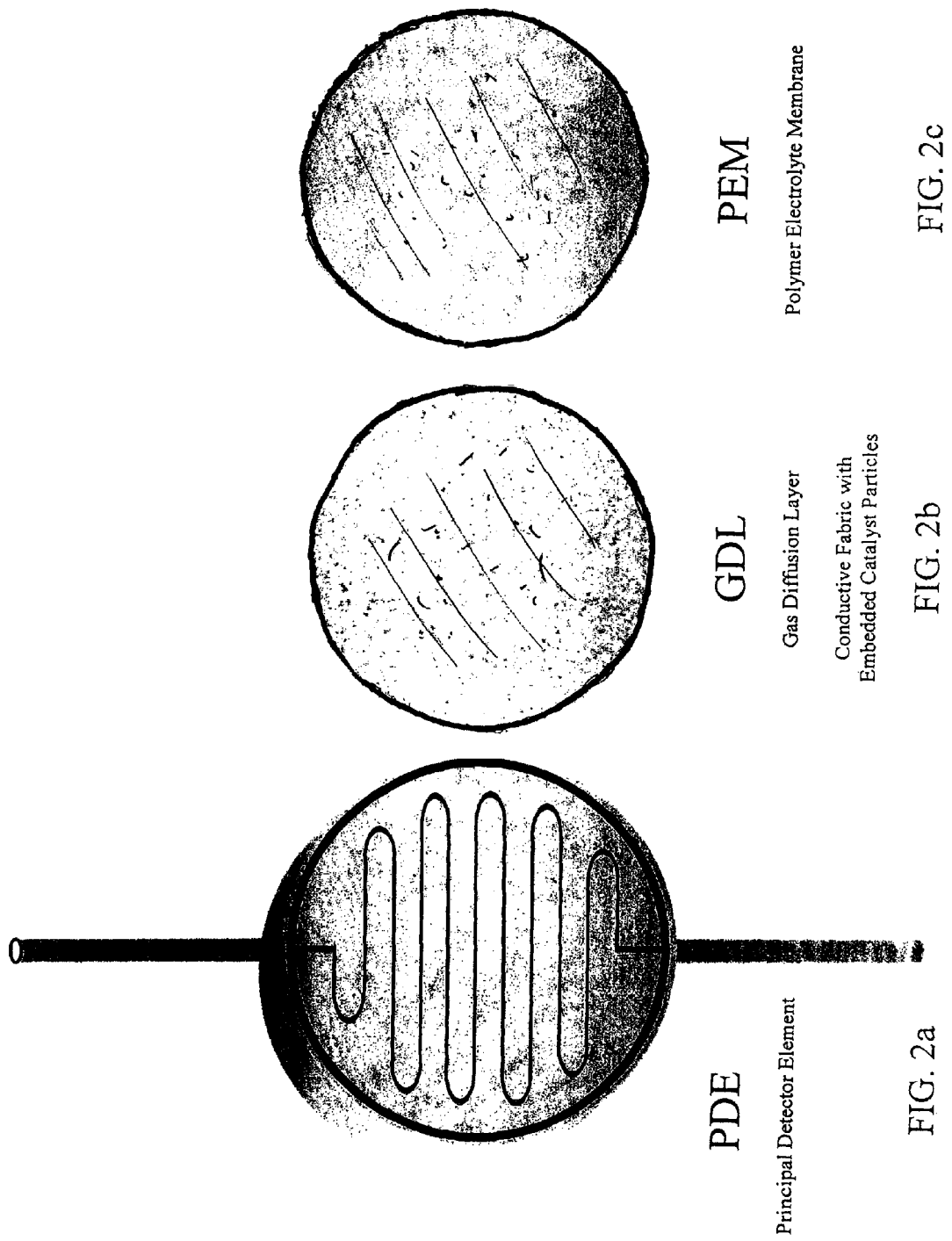
FIG. 2c PEM Polymer Electrolyte Membrane
FIG. 2b GDL Gas Diffusion Layer Conductive Fabric with Embedded Catalyst Particles
FIG. 2a PDE Principal Detector Element

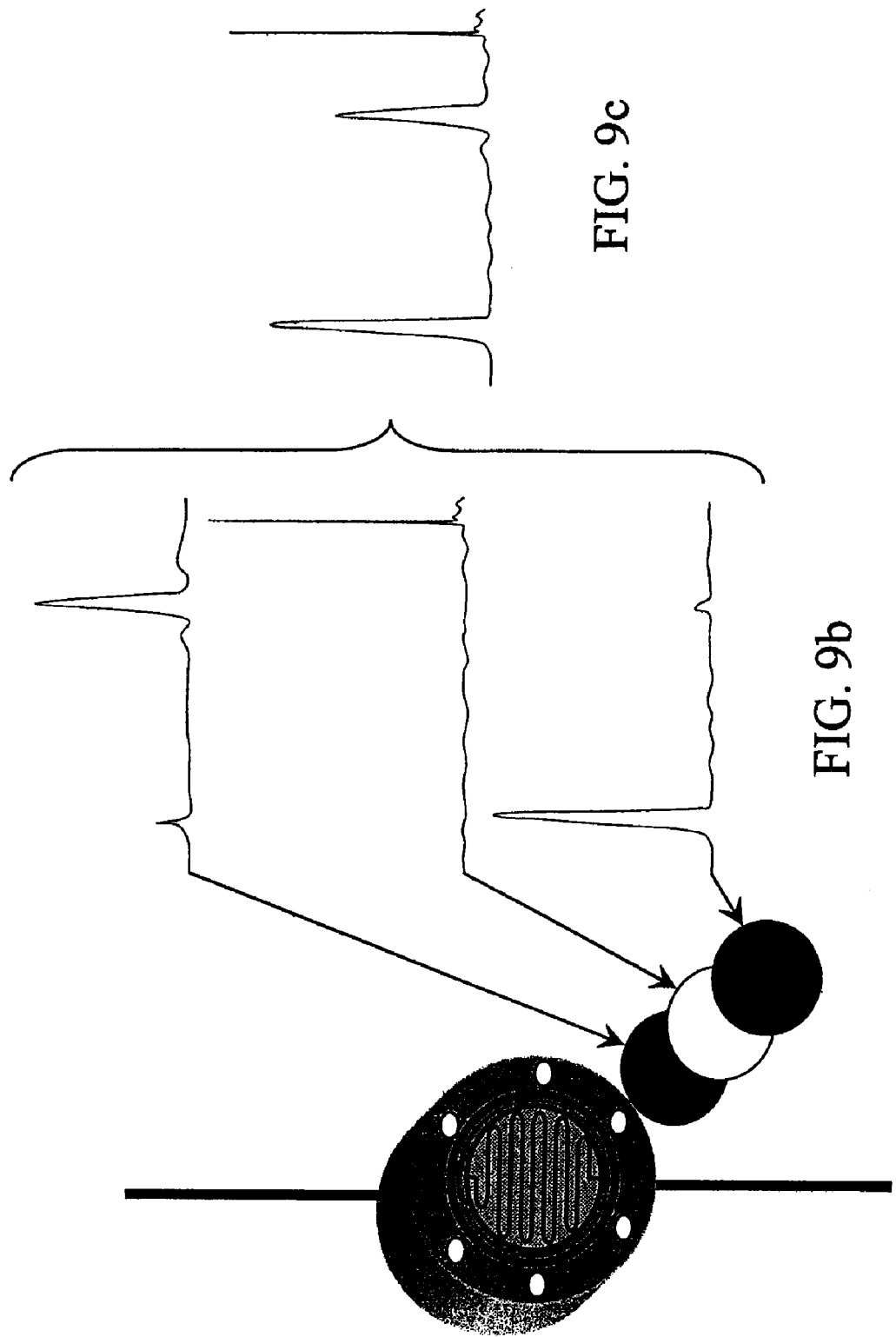

NMR APPARATUS FOR IN SITU ANALYSIS OF FUEL CELLS

RELATION TO OTHER PATENT APPLICATIONS

The present Non Provisional application relates to and claims priority of U.S. Provisional Patent Application No. 60/859,659 filed on Nov. 17, 2006, which is hereby incorporated by reference in its entirety.

CONTRACTUAL ORIGIN OF THE INVENTION

The United States Government has rights in this invention pursuant to Contract No. W-31-109-ENG-38 between the United States Government and the University of Chicago and/or pursuant to Contract No. DE-AC02-06CH11357 between the United States Government and U. Chicago Argonne, LLC representing Argonne National Laboratory.

FIELD OF THE INVENTION

This invention relates to a device, which allows for the in situ analysis of an operating fuel cell under real conditions (this is known as an "operando" device/method).

BACKGROUND OF THE INVENTION

Monitoring the events taking place in fuel cell systems (and fuel cell materials) under operating conditions is crucial for understanding the reaction mechanisms of many important chemical processes (e.g., catalyst degradation, membrane breakdown) and physical processes (e.g., water transport and distribution), and would allow the rational design of new or better fuel cells and fuel cell materials (e.g., catalysts and membranes). Operando methodology combines the evaluation of new materials (activity, selectivity of catalysts; and hydration, conductivity of membranes) and fuel cell system performance (flow, distribution of water) in a single experiment. Operando methodologies appear as an excellent tool to assess the structure-reactivity relationships at a molecular scale since structural and catalytic parameters are determined simultaneously. Furthermore, studies of fuel cells under actual operating conditions allows for a detailed understanding of temperature, loading, and design.

SUMMARY OF THE INVENTION

Operando Spectroscopy and Imaging using the Fuel Cell Toroid Cavity Detector invention disclosed in U.S. Pat. Nos. 6,469,507 B1, 6,674,283 B2 and 6,774,635 B1, the disclosures of which are incorporated herein, provides a unique and versatile approach for developing and adapting new spectroscopic techniques for studies of fuel cell materials and systems under real and close-to-real operating conditions.

Accordingly, it is an object of the present invention to provide a fuel cell toroid cavity detector for in situ analysis of samples through the use of nuclear magnetic resonance, the toroid cavity detector comprising: a gas-tight housing forming a toroid cavity with a longitudinal axis along the diameter wherein the housing is disposed in an externally applied magnetic field $B_0$ and contains samples to be analyzed; a first electrical conductor hollow conduit extending through the housing along the longitudinal axis into the toroid cavity; a principal detector element contained within the toroid cavity connected to the first electrical conductor hollow conduit; a second electrical conductor hollow conduit connected to the principal detector element and extending along the central longitudinal axis of the housing; the principal detector element comprising a generally flat metal conductor having a plane that is oriented generally parallel to the longitudinal axis of the toroid cavity, the metal conductor being disposed adjacent to the sample and having a predefined shape for the sample; a fuel cell disposed within the toroid cavity detector and containing the samples; and an NMR spectrometer electrically coupled and applying a radiofrequency excitation signal pulse through the first and second electrical conductor hollow conduits and the principal detector element for producing a radiofrequency magnetic field $B_1$ in the samples and in the toroid cavity. The principal detector element is fitted with one or more coils of wire. The coils are energized with direct or alternating current to cause modulation of the magnetic field experienced by the sample. User-defined magnetic field modulations provide a means to selectively interrogate chemical reactions and chemical composition of the components of a fuel cell, including the anode, cathode, and membrane.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIGS. 1(a)-(e) show an exploded side and top view of the invention with both anode and cathode principal detector elements (PDE). The figures are read top to bottom and left to right;

FIGS. 2(a)-(c) show an exploded view of a principal detector element (PDE), a gas diffusion layer (GDL) catalyst-embedded fabric and a polymer electrolyte membrane (PEM);

DETAILED DESCRIPTION OF THE PREFERRED EMBODIMENT

Figure 3:
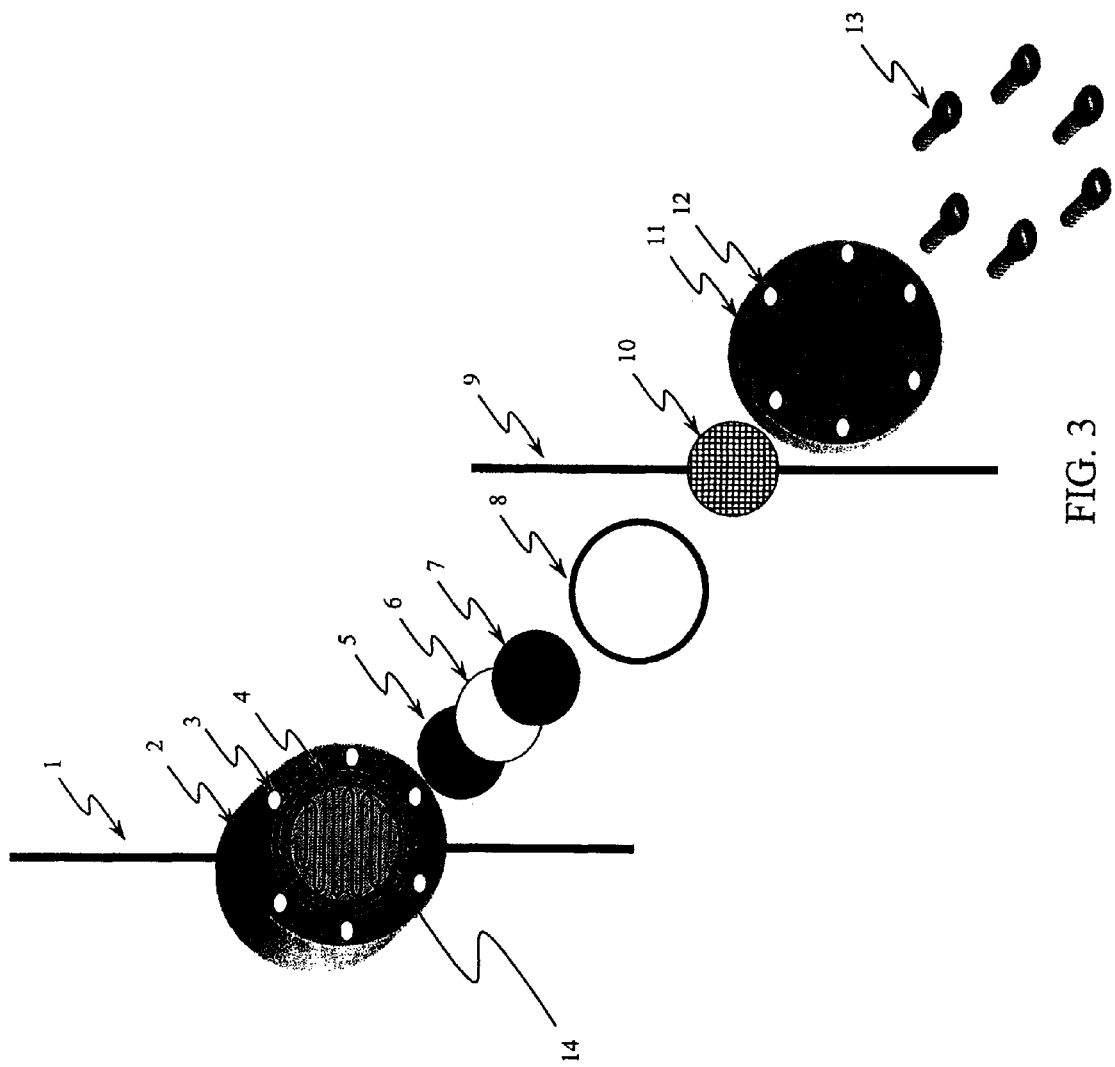
FIG. 3 is an exploded view of a PEM fuel cell combined with a specially constructed PDE.

New operando methodologies for advancing fuel cell designs using the Fuel Cell Toroid Cavity Detector invention provides a greater focus on the achievable objectives and key issues that limit modern fuel cells rather than on the continued application of currently available, but ineffective techniques.

What is critical to protect is a new principal detector element, PDE that was designed specifically for NMR/MRI of fuel cells and modified as hereinafter set forth to act as an electrode in a fuel cell, while functioning as the detector for NMR spectroscopy and imaging. As seen in FIGS. 1-9, the PDE consists of a circular disk and a top and bottom hollow tube metal conductor. The circular disk has engraved channels that snake back and forth from the top to the bottom. A top hollow tube metal conductor attaches to the top of the disk at the entrance to the channel system. A bottom hollow tube metal conductor attaches to the bottom of the disk at the exit of the channel system. The channel grooves are cut into the front face of the disk. The depth of the channels is a variable parameter and can range from 0.01 to 5 mm; preferably, 0.1 to 2 mm. The width of the channels is a variable parameter and can range from 0.01 to 5 mm; preferably, 0.1 to 1 mm. The channel should snake back and forth on the front face surface of the disk. The PDE is used as a means for saturating an electrode with a fuel feed, as a current collector for the same electrode, and as an inductor for sensing an NMR signal. All three functions of the PDE proceed simultaneously during fuel cell operation and operando studies. The channels are covered with an electrically conductive fabric material impregnated with catalyst particles as is well known in the art. Two similarly formed PDE/fabric assemblies are constructed; one for the anode, another for the cathode. The fabric contains different catalyst particles for the anode compared to the cathode, as is well known in the art. The two PDE/fabric assemblies are pressed together, front faces and fabrics facing each other, with a proton conducting membrane placed in between. A gasket or o-ring is positioned on the perimeter of the PDE to affect a hermetic seal. The back sides of the PDEs are fitted with wire coils. The wire coils are energized with alternating or direct current to cause modulation of the magnetic field experienced by the internal components of the fuel cell. Nuclear magnetic resonance (NMR) spectroscopy and imaging methods utilize magnetic field modulations to interrogate chemical reactions and transport phenomenon that take place at different locations within the fuel cell.

An important aspect of the invention is the PDE that serves multiple functions, including those needed for fuel cell operation, but more importantly, also those functions that are essential for NMR spectroscopy and imaging.

The PDE is made of an electrically conductive material, including copper, aluminum, stainless steel (and other partially-ferrous metals) graphite, and various alloys. The PDE can be made of a non-electrically conductive material, such as glass, quartz, Teflon, Vespel, Peek, Torlon, and other polymers and coated with an electrically conductive material. The coating process can be achieved by chemical vapor deposition, electrospray, painting, or other means, well known in the art.

Another important aspect of the invention is the utilization of materials with magnetic properties for fabricating PDEs that modify the local static magnetic field at the front face of the PDE for conducting spatially localized NMR/MRI. Another aspect of the invention is the housing for the Fuel Cell Toroid Cavity Detector. The housing is made of a mechanically-rigid material that is suitable for a fuel cell housing. A conductive coating can be applied to the exterior surface of electrically non-conducting housings for proper toroid cavity operation.

Figure 4:
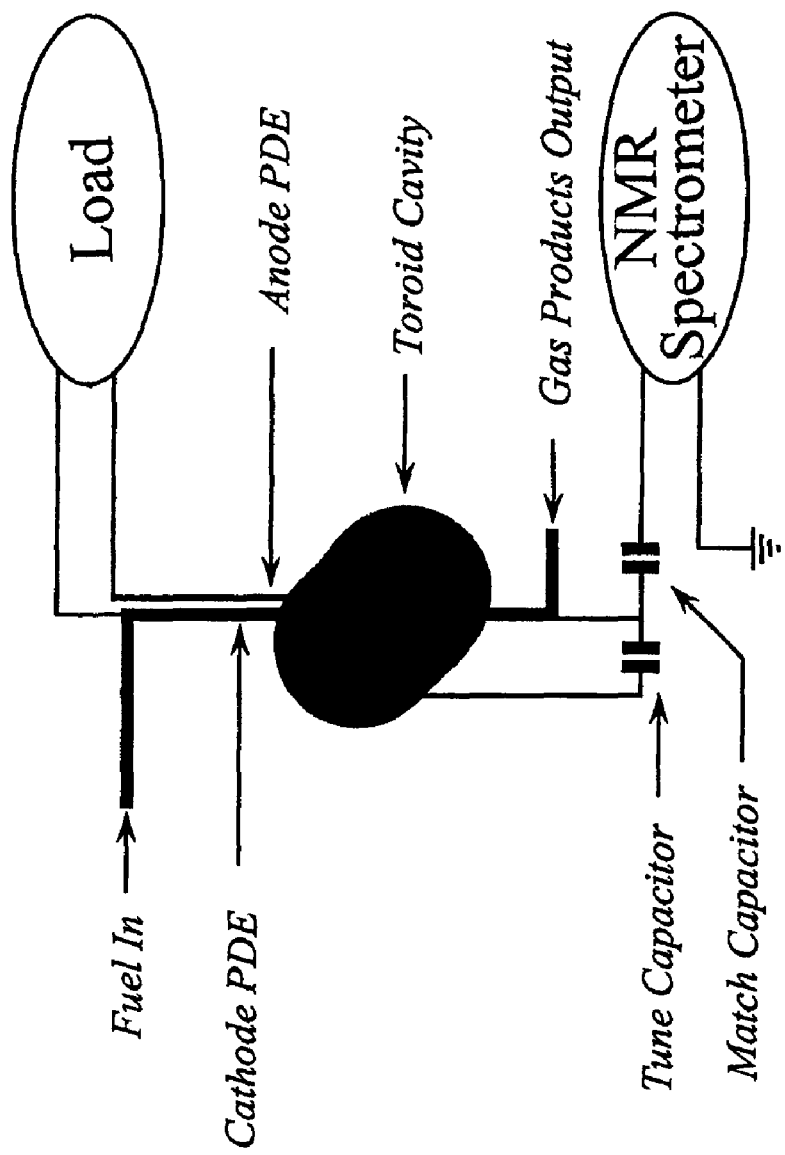
FIG. 4 is a schematic diagram showing operation of a fuel cell under load and PDEs simultaneously connected to NMR Spectrometer and Load.

The present invention includes those components of a fuel cell already known in the art. Thus, a fabric material that has a graphitic electrically conductive coating embedded with platinum catalyst particles may be employed as a gas diffusion layer (GDL) for the cathode, see FIG. 1(b) and FIG. 2(b). The catalyst-embedded fabrics used at the cathode and at the anode are materials that are commercially available. The polymer electrolyte membrane (PEM) is also commercially available (e.g., Nafion). The current collector element of a fuel cell and channel system are also know in the art. The present invention relates to the combination of a current collector with channel system that can be used on either or both of the cathode and anode side of the fuel cell that has the additional unique function of a principal detector element (PDE). The PDE together with a few capacitors forms an LC circuit that can be tuned to excite nuclei and detect NMR signals (like an antenna in a radio that can be tuned to a radio station). The PDE is a disk of a conductive material (e.g., copper) that has a channel system for the flow of a gas that is required for fuel cell operation. The connection of the PDE to a few capacitors makes it possible to use it also for NMR/MRI detection. The invention includes a container that holds all the components of a fuel cell in a hermetically sealed reaction chamber. The container is also used as the structure for the NMR/MRI toroid cavity detector (TCD). That is, the container is also part of the circuit of the TCD. A disassembled (FIG. 3) and an assembled (FIG. 4) FCTCD are shown. FIG. 4 shows the assembled TCD and the RF circuit design to enable NMR/MRI measurements. FIG. 3 depicts an exploded view of the invention. The following components of the cited invention in FIG. 3 are itemized:

1 is an electrically conductive hollow tube;
2 depicts the cell container body which is made of metal (stainless steel or aluminum);
3 references threaded holes used to fasten the cover item 11;
4 is a machined o-ring groove to combine with o-ring 8 to form a hermetic seal after instillation of the other components;
5 is a cathode graphitic fabric disk embedded with catalyst particles;
6 illustrates the polymer electrolyte membrane (PEM);
7 is a anode graphitic fabric embedded with catalyst particles;
9 is an electrically conductive hollow tube for gas product egress;
10 is the current collector and channel system for anode (can be a second PDE);
12 and 13 are the means for fastening the cover;
14 is the current collector disk with a channel system for cathode and PDE.

Figures 5A, 5B:
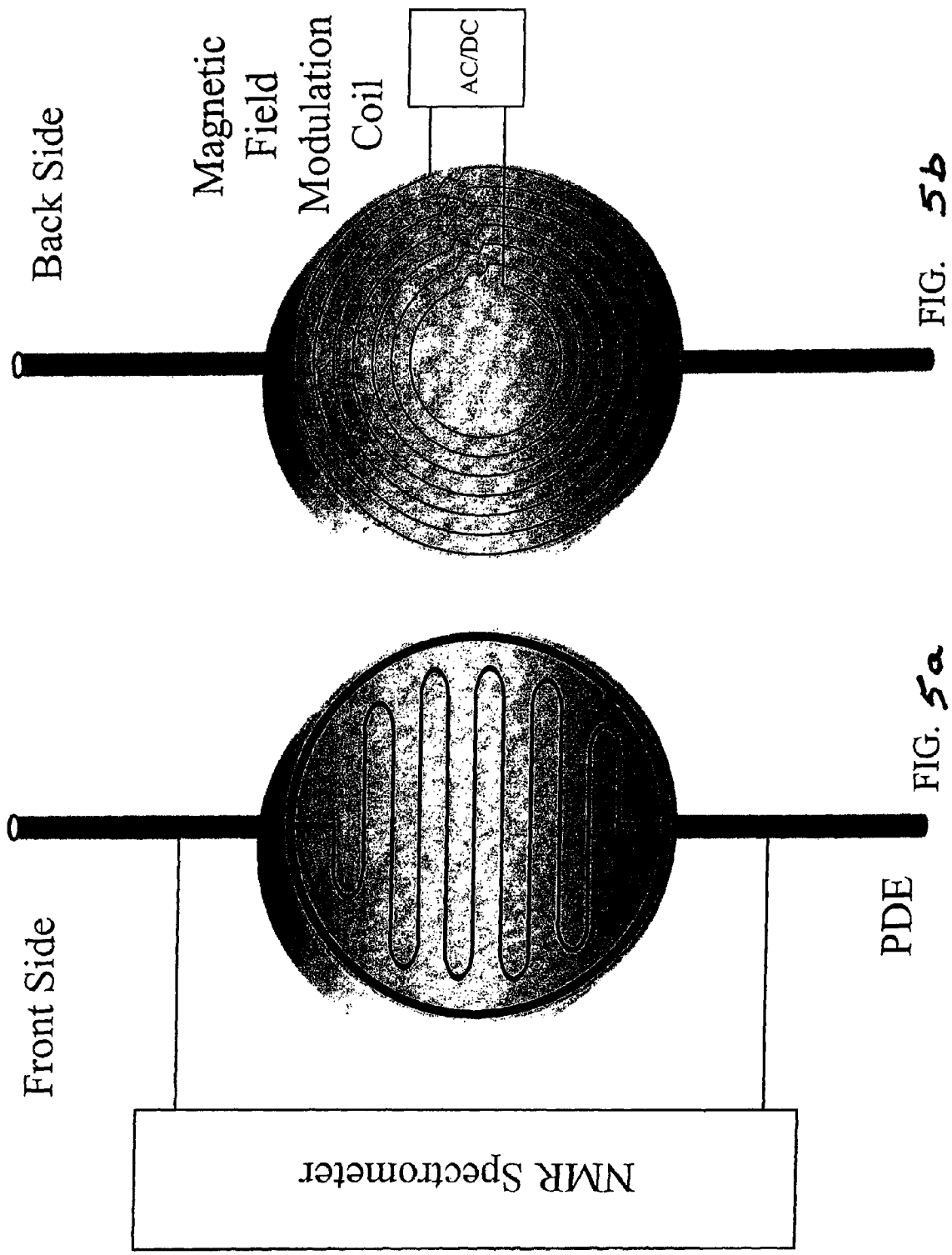
FIGS. 5(a)-(b) show details of the front and back sides of the principal detector element in the invention.
Figure 6:
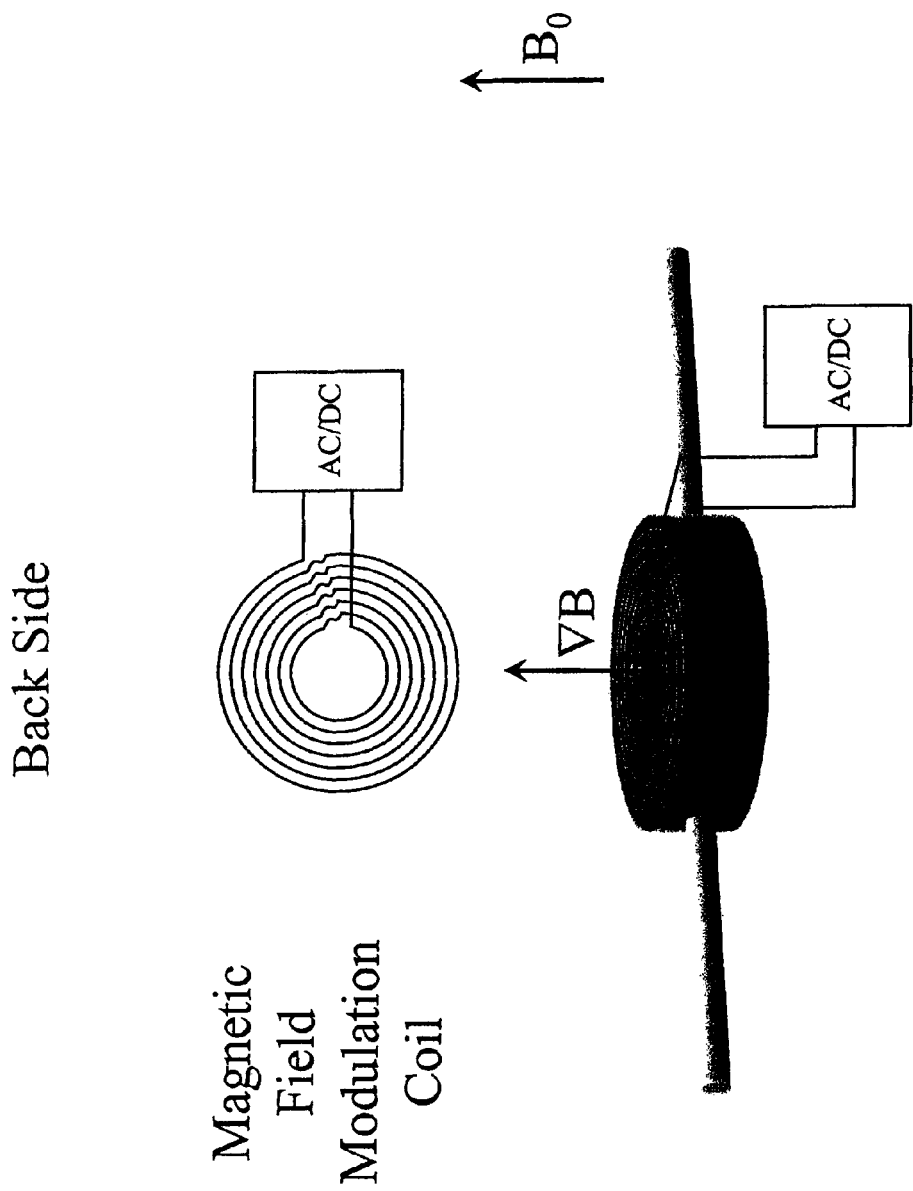
FIG. 6 illustrates the principal detector element having power applied and subject to a magnetic field FIG. 7 show the interconnections of the electronic components of the invention for operation as a nuclear magnetic resonance detector.

FIGS. 5(a)-(b) illustrate the PDE of the Fuel Cell TCD (toroid cavity detector) with the PDE described in the front profile and the back side having an embedded coil. FIG. 6 illustrates the apparatus of FIG. 5(a)-(b) connected to a power source and subjected to a magnetic field.

Figure 7:
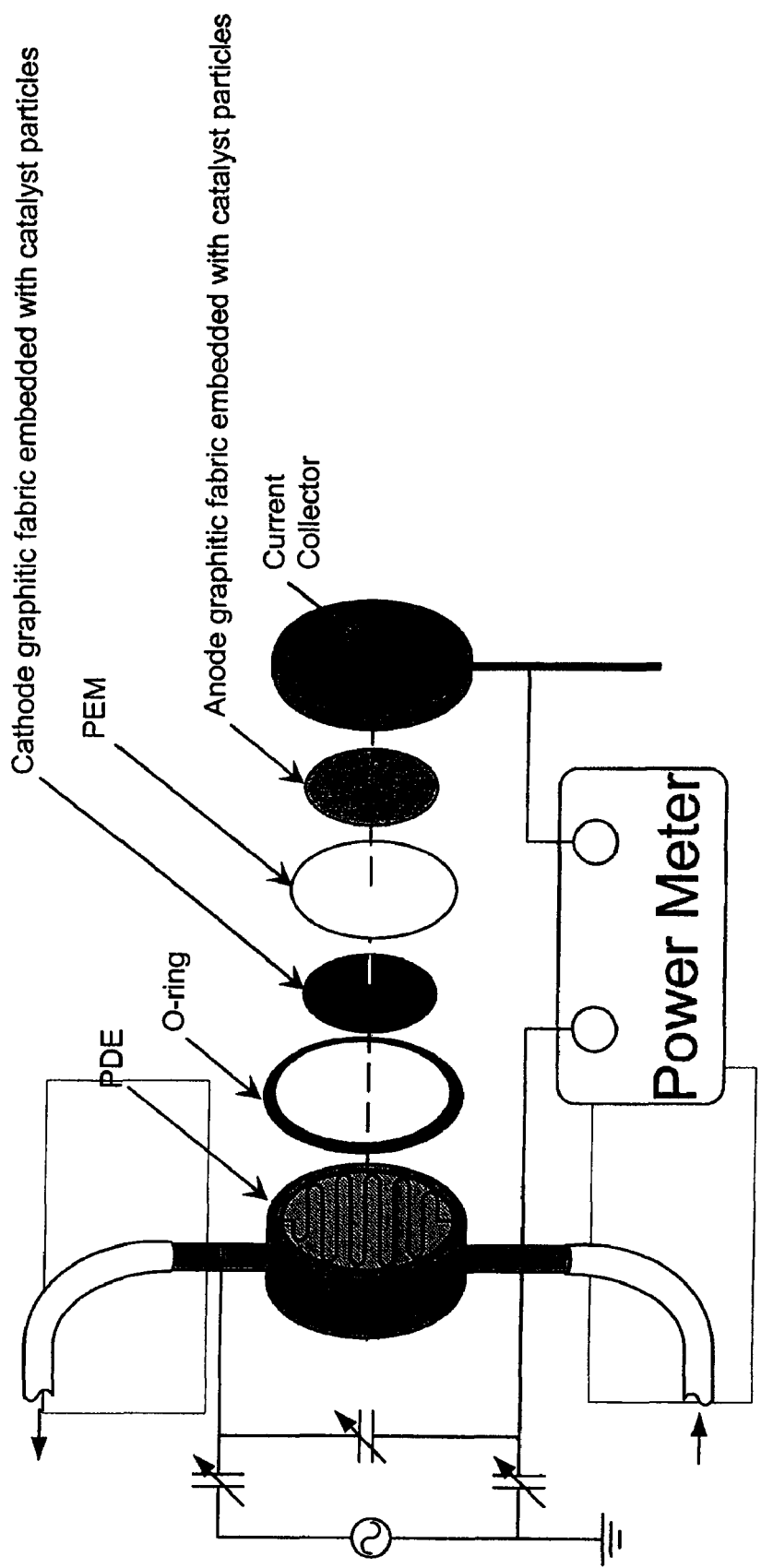

FIGS. 6 (a)-(c) illustrate the PDE of the Fuel Cell TCD (toroid cavity detector) with the PDE described in the front profile and the back side having an embeded coil connected to a power source. Thus, basically, the fuel cell TCD (toroid cavity detector) has two essential elements: 1. the principal detector element (PDE) and 2. an embedded coil in the PDE which is used to modulate the external magnetic field. FIG. 7 illustrates the fuel cell detector in association with an radiofrequency (RF) oscillator circuit having tuning capacitors connected to a transcoupler of an NMR spectrometer also illustrated is the fuel cell detector in simultaneous association with a power meter, used to measure the output power of the fuel cell.

Figure 8D:
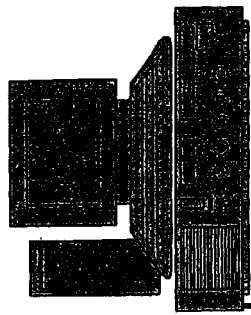
FIGS. 8(a)-(e) show the interconnections of the components of the invention for in situ studies of fuel cells while under actual operational conditions; and, FIGS. 9(a)-(c) show the spatial separation of spectroscopic data obtained from different internal components of a fuel cell.
Figure 8E:
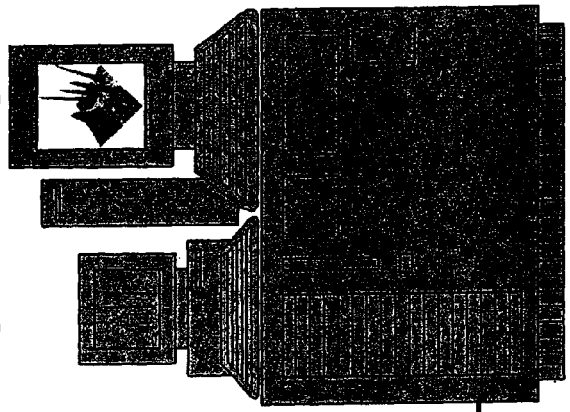
Figure 8C:
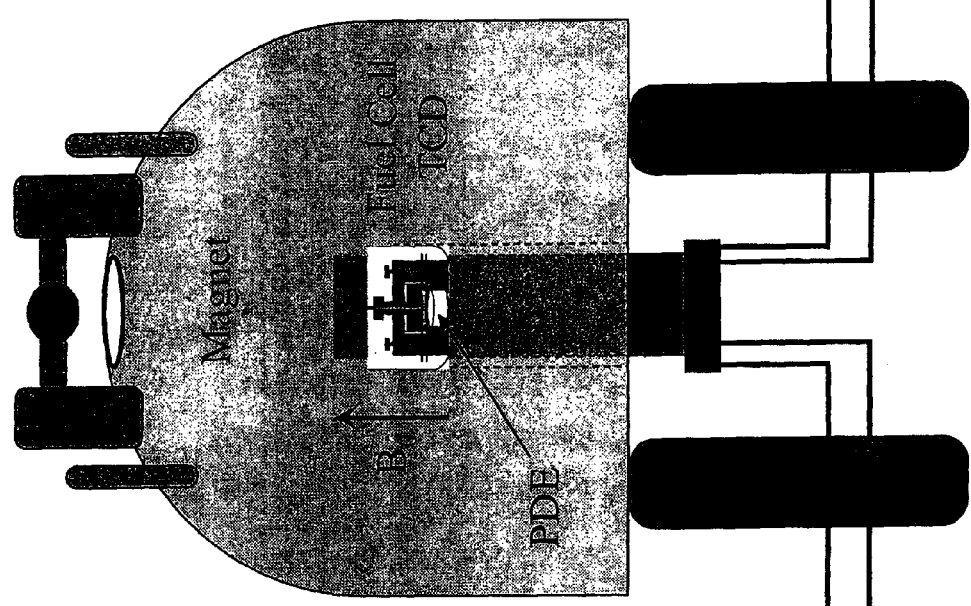
Figure 8A:
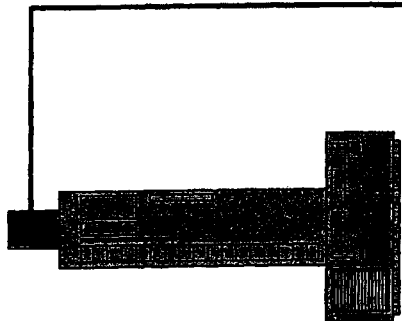
Figure 8B:
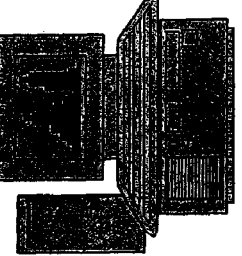

FIGS. 8(a)-(e) illustrate the interconnections of the components of the invention for in situ studies of fuel cells while under actual operational conditions. FIG. 8(c) shows the position of the Fuel Cell TCD within the commercial superconducting magnet used for NMR spectroscopy and imaging. The longitudinal axis of the PDE of the Fuel Cell TCD can be oriented so that it is parallel, perpendicular, or at any other angle with respect to the external magnetic field direction. For the superconducting magnet shown, the direction of the field is parallel to the vertical direction. The center bore of the magnet is 89 mm in diameter and spance the length of the magnet container, approximately 4 feet long; the Fuel Cell TCD with associated electrical wired and tubing is accommodated within the magnet bore. The Fuel Cell TCD is connected to and operated by a Fuel Pump (FIG. 8(a)) and a Fuel Cell Controller (FIG. 8(b)). Elctrochemical fuel cell performance data is collected by the Elctrochemistry Fuel Cell Monitor (FIG. 8(d)). In situ spectroscopic and imaging analyses of the fuel cell, while it is operating, is performed by the NMR Spectrometer/Imager (FIG. 8(e)).

FIG. 9 (a) illustrates the PDE of the Fuel Cell TCD adjacent to a series of disks comprising the anode, proton-conducting membrane, and cathode of a fuel cell. FIG. 9 (b) shows the NMR spectra recorded for the individual disk components of the fuel cell by application of Fuel Cell TCD imaging methods. FIG. 9 (c) shows the composite spectral data that would be obtained from the fuel cell without the application of the Fuel Cell TCD imaging capability. The Fuel Cell TCD provides spatial separation of NMR spectroscopic data obtained from different internal components of a fuel cell.

As noted previously, the PDE is a solid disk fitted with inlet and outlet tubes. The front side of the PDE is fitted with a sinusoidal groove that is connected at the entrance and outlet metal tubes, respectively. The sinusoid groove becomes a sunusoid chamber when the front side of the PDE is covered with a material (e.g. fabric—FIG. 3). The purpose of the sinusoid groove is to transport a fluid (e.g., hydrogen or methanol) so that is saturates the cover material with a molecular source of protons for fuel cell operation. The sinusoid groove or channel can also serve to remove molecular byproducts from a fuel cell operation. As was noted, the PDE is formed of a material that is electrically conductive and that provides a local magnetic field distortion near the front side face when it is placed in a strong magnetic field. The back side of the PDE is fitted with a coil of wire. The coil is energized with direct or alternating current to cause the modulation of the magnetic field near the face of the front side. The PDE also functions as an inductor in a radiofrequency oscillator circuit detector for performing nuclear magnetic resonance spectroscopy and imaging experiments. In one embodiment of the invention, the front side face of a copper anode PDE is made of a 0.2 mm-thick disk of rhodium metal. The susceptibility of the rhodium metal causes a large distortion of the external static magnetic field $B0$ within the Fuel Cell TCD container; the distortion is greatest near the anode gas diffusion layer, resulting in a severely distorted and useless NMR spectrum of the anode. A 20-turn coil of 22 gauge Teflon-coated wire, attached to the backside of the copper anode PDE, is energized with 200 mA of direct current causing the generation of a static magnetic field gradient $?B0$. The static magnetic field gradient counteracts the local magnetic field distortion adjacent to the anode caused by the rhodium; the result is a localized homogeneous magnetic field at the anode. The magnetic field gradient generated by the coil is not of sufficient magnitude to undo the magnetic field distortions at other locations in the fuel cell (e.g., the locations of the membrane and cathode disks). Therefore, a spatially selective and useful high-resolution NMR spectrum of the anode is recorded by energizing the anode PDE with a single 20 microsecond, 2.0 amp pulse of 300 MHz radiofrequency energy; the NMR signals from the polymer electrolyte membrane and the cathode gas diffusion layer are so distorted that they are rendered invisible. The spatially selective interrogation of the anode by NMR spectroscopy without interference from membrane and cathode NMR signals provides a non-invasive means to selectively study anode performance in a fuel cell under actual operating conditions. The advantage of the FCTCD invention over competative MRI devices is simplicity and speed. The FCTCD invention requires a single short pulse to interrogate a component of the fuel cell (e.g., the anode) whereas competative devices require many pulses and are therefore limited to less frequent and slow interrogations.

It should be noted that the current collector channel system can be used on the cathode or anode side of the fuel cell while having the additional function of serving as a principal detector element (PDE). As is illustrated in FIG. 4, the PDE together with select capacitors forms an LC circuit that can be tuned to excite nuclei and detect NMR signals (like an antenna in a radio that can be tuned to a radio station). As noted earlier, the PDE is a disk of conductive material (e.g. copper) that has a channel for containing the flow of gas that is required for fuel cell operation. The combination of the PDE and the capacitive network allows for its use in NMR/MRI detection. As is shown in FIG. 3 the system forms a cell which contains all of the components of a fuel cell in a hermetically sealed chamber. The container of FIG. 3 is also used as the probe structure for the NMR/MRI toroid cavity detector (TCD). That is the container is part of the circuit of the TCD. The assembled TCD includes the RF circuit components for affecting NMR/MRI measurements.

While the invention has been particularly shown and described with reference to a preferred embodiment hereof, it will be understood by those skilled in the art that several changes in form and detail may be made without departing from the spirit and scope of the invention.

The embodiments of the invention in which an exclusive property or privilege is claimed are defined as follows:

1. A fuel cell toroid cavity detector for in situ analysis of a operational fuel cell using nuclear magnetic resonance/nuclear magnetic imaging comprising:
   a sealed container housing where said housing is electrically conductive and where a sealed chamber of said housing penetrates a first surface of said housing but not an opposing second surface of said housing,
   an electrically conductive first hollow tube which penetrates a side wall of said housing extending into said chamber for transporting fuel into said chamber,
   an electrically conductive second hollow tube which is approximately position in opposition to said first tube and also penetrates from said chamber through said side wall and acts as a first exit port,
   a first principal detector element which is sized to fit in said chamber and where said first detector element has a oscillating channel positioned on a first surface of said electrically conductive first detector element and where said first surface is exposed to an open end of said chamber and where a first end of said channel is in fluid connection with said first hollow tube and where a second end of said channel is in fluid connection with said second hollow tube and where said first detector element functions as a cathode,
   a cathode fabric which is embedded with catalyst particles and is adjacent to said channels of said first principal detector element and is sized to correspond to an exposed surface of said first principal detector, a polymer electrolyte membrane which is of similar size to said cathode fabric and is outwardly adjacent to said cathode fabric, an anode fabric embedded with catalyst particles and sized in a manner similar to said polymer electrolyte membrane and which is positioned adjacent to and outward to said polymer membrane, a current collector which can be a second principal detector element which functions as an anode and is positioned adjacent to and outward from said anode fabric, an electrically conductive hollow third tube which is in fluid connection with said current collector and serves as a gas transport duct, an electrically conductive hollow forth tube which is in fluid connection with said current collector and serves as an gas export duct, a cover plate which is attached to an outer surface of said chamber and forms an external cover to said chamber, a means for hermetically sealing said fuel cell toroid detector, a means for connecting said detector to an RF circuit and a means for modulating an external magnetic field.

2. The detector of claim 1 where said modulating means is a conductive coil attached or proximate to a exposed surface of said detector where said surface is in opposition to said cover plate.

3. The detector of claim 2 where said coil is energized with either a direct or alternating current source.

4. The detector of claim 1 where said RF circuit is electrically coupled to said first hollow tube and said current collector.

5. The detector of claim 4 where said RF circuit includes an NMR spectrometer.

6. The detector of claim 1 where said sealing means due to a seated o-ring between said container housing and said cap.

* * * * *